US006929398B1

(12) United States Patent
Tybinkowski et al.

(10) Patent No.: US 6,929,398 B1
(45) Date of Patent: Aug. 16, 2005

(54) TWO-PIECE PALLET ASSEMBLY FOR PATIENT TABLE

(75) Inventors: Andrew P. Tybinkowski, Boxford, MA (US); Robert F. Riemer, Andover, MA (US); Robert M. Williams, Wilmington, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/379,351

(22) Filed: Mar. 4, 2003

Related U.S. Application Data (60) Provisional application No. 60/395,122, filed on Jul. 11, 2002.

(51) Int. Cl.[7] .............................. A61B 6/04; A61B 5/05
(52) U.S. Cl. ......................... 378/209; 600/415; 5/601
(58) Field of Search ........................... 5/600, 601, 611, 5/943; 378/209; 600/415

(56) References Cited

U.S. PATENT DOCUMENTS 3,757,129 A * 9/1973 Hogan ........................ 5/601
3,944,204 A * 3/1976 Cesar ......................... 5/601

* cited by examiner

*Primary Examiner*—Michael Safavi
(74) *Attorney, Agent, or Firm*—McDermott Will & Emery LLP (57) ABSTRACT

A patient table including a table assembly and a pallet assembly supported on the table assembly. The pallet assembly includes a longitudinally extending lower portion that is longitudinally moveable with respect to the table assembly and has opposing ends that are laterally fixed with respect to the table assembly. The pallet assembly also includes a longitudinally extending upper portion that is longitudinally fixed with respect to the lower portion of the pallet assembly and has opposing ends that are each laterally moveable with respect to the ends of the lower portion. Among other features and advantages, a pallet assembly constructed in accordance with the present invention has opposing ends that are each laterally adjustable so that a patient lying on the pallet can be correctly positioned within medical diagnostic and therapy systems in a comfortable manner, and without being moved on the pallet.

9 Claims, 8 Drawing Sheets

TWO-PIECE PALLET ASSEMBLY FOR PATIENT TABLE

CROSS-REFERENCE TO RELATED APPLICATIONS

The present application claims priority to co-pending provisional U.S. patent application Ser. No. 60/395,122, which was filed on Jul. 11, 2002, is assigned to the assignee of the present application, and is incorporated herein by reference.

FIELD OF THE INVENTION

The present invention relates generally to radiation therapy systems and, more particularly, to a table for supporting a sample, such as a patient, in a radiation therapy scanner during a radiation therapy procedure. Even more particularly, the present invention relates to a two-piece pallet assembly for a patient table, wherein opposing ends of the pallet assembly are laterally adjustable.

BACKGROUND OF THE INVENTION

Medical diagnostic imaging and scanner systems such as magnetic resonance imaging (MRI) apparatus, X-ray machines, positron emission tomography (PET) scanners, and computer tomography (CT) scanners are well known. Such machines are quite popular as a tool for providing images of internal portions of patients for diagnosis of medical conditions, such as internal injuries, cancerous tumors and the like. Owing to good quality tomographic images with low dosage X-ray radiation, the CT scanner has become especially well accepted by the medical profession for examining patients and diagnosing medical conditions.

An annular gantry normally supports many of the components of a CT scanner and includes an outer ring secured to a stand and an inner ring mounted for rotation within the outer ring. During a scanning procedure, a pallet of a patient table is extended through the center of the gantry and the inner ring is rotated about the pallet. A patient lies on the pallet within the center of the gantry during the scanning procedure. The components supported by the gantry can include an x-ray tube for providing the x-ray beam, one or more high voltage power supplies, balancing weights, a data acquisition module, and a bank of detectors diametrically opposed from the x-ray source. At least some of these components are secured in the inner ring for rotation therewith.

In order to obtain tomographic images of a patient with a CT scanner or X-ray CT apparatus, it is necessary that the patient be located exactly at a predetermined position inside the opening of an annular scan gantry of the apparatus. For this reason, such apparatus has been provided with a patient handling couch or table which has a table assembly that is moveable vertically to be in line with an axis of rotation of the scan gantry (such that a longitudinal center line of the patient table is in alignment with the axis of rotation of the scan gantry), and a pallet that supports the patient and is moveable horizontally, or axially in and out of the scan gantry, parallel with the axis of rotation.

Tomotherapy is a new way to deliver radiation treatment for cancer. It delivers a very sophisticated form of IMRT, or intensity modulated radiotherapy, and integrates treatment planning, patient positioning, and treatment delivery in one system. Radiation is one of the most effective cancer treatments available. It works by damaging the cells it strikes: when the cancer cells are damaged enough, they will die. But what happens to healthy cells that are struck by the radiation beam? The key factor for radiotherapy is that healthy cells can repair themselves better than cancer cells. That's why radiotherapy treatments are divided into many treatments, or fractions, over several weeks. Delivering a little radiation to the tumor area every day gives healthy cells time to recover between each session, while causing unrepairable damage to more and more cancer cells.

Radiation treatment is also usually directed at the tumor from several different directions, so that more radiation is targeted on the tumor, but a lesser dose is spread over the surrounding healthy tissue. Even though normal tissue can recover from exposure to radiation, there are often side effects, and of course too much radiation can damage normal tissue beyond repair. Until recently, it was very difficult for doctors to deliver enough radiation to kill a tumor without causing painful or debilitating side effects. Some side effects might go away once the treatment is complete, but others could continue to affect quality of life for years.

Of course, one of the goals of any radiation therapy is to avoid healthy tissue as much as possible, but some healthy cells will be damaged by the radiation treatment. So doctors and scientists have begun to look for better ways to deliver enough radiation to the tumor, while sparing normal tissue as much as possible. One of the most promising methods is IMRT, or intensity modulated radiotherapy.

IMRT is one of the most important recent advances in radiation therapy. The goal of IMRT is to change (modulate) the size, shape, and strength of the radiation beam in order to focus enough dose on the tumor to kill the cancer cells, while sparing as much as possible the surrounding healthy tissue. There are different ways to change the size, shape, and strength of the radiation beam. For example, custom radiation filters called compensators can be used to modulate the radiation beam. But compensators are costly and time-consuming to make, and involve very complicated setup and delivery procedures.

A more promising device for IMRT is called a multileaf collimator, or MLC, which is a device that is attached to the linear accelerator. An MLC is made of many individual fingers or leaves, which move across the beam in a specified pattern to block or allow the passage of radiation, shaping the beam as it is emitted.

Like conventional radiotherapy, conventional IMRT is usually delivered from several different directions (usually 5 to 9, although sometimes as many as 13). The greater the number of beam directions, the more the high dose will be confined to the tumor, and the less chance for debilitating side effects. But conventional IMRT requires a lengthy and complicated setup process for each treatment fraction, and more beam directions requires more time for each treatment fraction.

The Hi-Art system, which has been developed by Tomo-Therapy™ Inc. of Madison, Wis. in association with the Tomotherapy Research Group of the University of Wisconsin, Madison, takes IMRT one step further, combining a very sophisticated MLC with a unique helical delivery pattern in order to deliver precise radiation at the target. Instead of delivering radiation from just a few directions, the Hi-Art system delivers radiation from every point on the helix, in about the same amount of time as conventional IMRT.

The TomoTherapy Hi-Art System combines treatment planning, patient positioning, and treatment delivery into one system, in order to deliver precise treatment doses without increasing the radiation deposited on healthy tissue. Before beginning tomotherapy treatment, the doctor uses 3-D images (for example, from a computed tomography (CT) scanner) and special software to establish the precise contours for each region of interest (tumor) and any regions at risk (sensitive organs or structures). The doctor decides how much radiation the tumor should receive, as well as acceptable levels for surrounding structures. Then the Hi Art system calculates the appropriate pattern, position, and intensity of the radiation beam to be delivered, to match the doctor's prescription as closely as possible.

The Hi-Art system will allow doctors to take a special CT scan just before each treatment, so they can verify the position of the tumor, and adjust the patient's position if necessary to make sure the radiation is directed right where it should be. The Hi-Art system combines IMRT with a helical (or spiral) delivery pattern to deliver the radiation treatment. Photon radiation is produced by a linear accelerator (or linac for short), which travels in multiple circles all the way around the gantry ring. The linac moves in unison with a device called a multileaf collimator, or MLC. The computer-controlled MLC has two sets of interlaced leaves that move in and out very quickly to constantly modulate the radiation beam as it leaves the accelerator. Meanwhile, the couch or patient table is also moving, guiding the patient slowly through the center of the ring, so each time the linac comes around, it's directing the beam at a slightly different plane.

What is still desired, however, is a new and improved patient table for use with medical diagnostic imaging and scanner systems, such as tomography scanners, and medical treatment systems, such as radiation therapy systems. In particular, what is desired is a patient table including a longitudinally extending pallet having opposing ends that are each laterally adjustable. Among other features and advantages, the new and improved pallet will allow a patient lying on the pallet to be correctly positioned in medical diagnostic and medical treatment systems in a comfortable manner, and without being moved on the pallet. Such a new and improved pallet is particularly desirable for use with a radiation therapy system, such as the TomoTherapy Hi-Art System for example.

SUMMARY OF THE INVENTION

The present invention provide a new and improved pallet assembly for a patient table. A patient table constructed in accordance with the present invention can be used for, but is not limited to, positioning a patient within an imaging gantry of a treatment system for radiation therapy.

According to one exemplary embodiment of the present invention, the patient table includes a table assembly and a pallet assembly mounted on the table assembly. The pallet assembly includes a longitudinally extending lower portion that is longitudinally moveable with respect to the table assembly and has opposing ends that are laterally fixed with respect to the table assembly. The pallet assembly also includes a longitudinally extending upper portion that is longitudinally fixed with respect to the lower portion of the pallet assembly and has opposing ends that are each laterally moveable with respect to the ends of the lower portion.

Among other features and advantages, a pallet assembly constructed in accordance with the present invention has opposing ends that are each laterally adjustable so that a patient lying on the pallet can be correctly positioned within a medical diagnostic or medical treatment system in a comfortable manner, and without being moved on the pallet. A pallet assembly constructed in accordance with the present invention is particularly useful for use with a radiation therapy system, such as the TomoTherapy Hi-Art system, in adjusting a patient's position if necessary to ensure that radiation is directed at cancerous tumors and not healthy tissue.

The foregoing and other features and advantages of the present invention will become more readily apparent from the following detailed description of the disclosure, as illustrated in the accompanying drawing.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
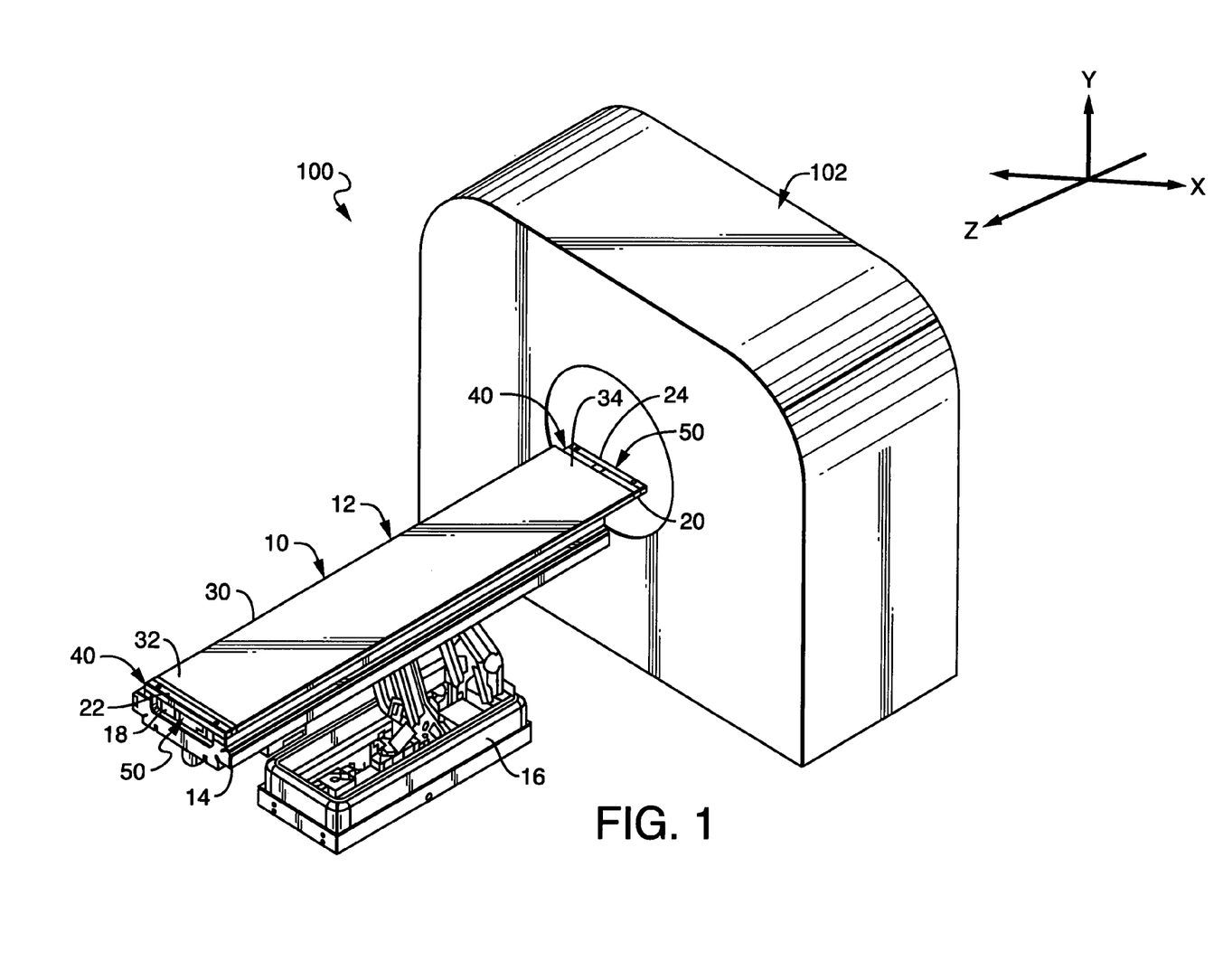
FIG. 1 is a top and end perspective view of an exemplary embodiment of a patient table including a pallet assembly constructed in accordance with the present invention, wherein the table is shown in a fully raised position and positioned with respect to a tomography scanner system such that a patient supported on a pallet assembly of the patient table would be generally aligned with an axis of rotation of a gantry of the tomography scanner system.
Figure 2:
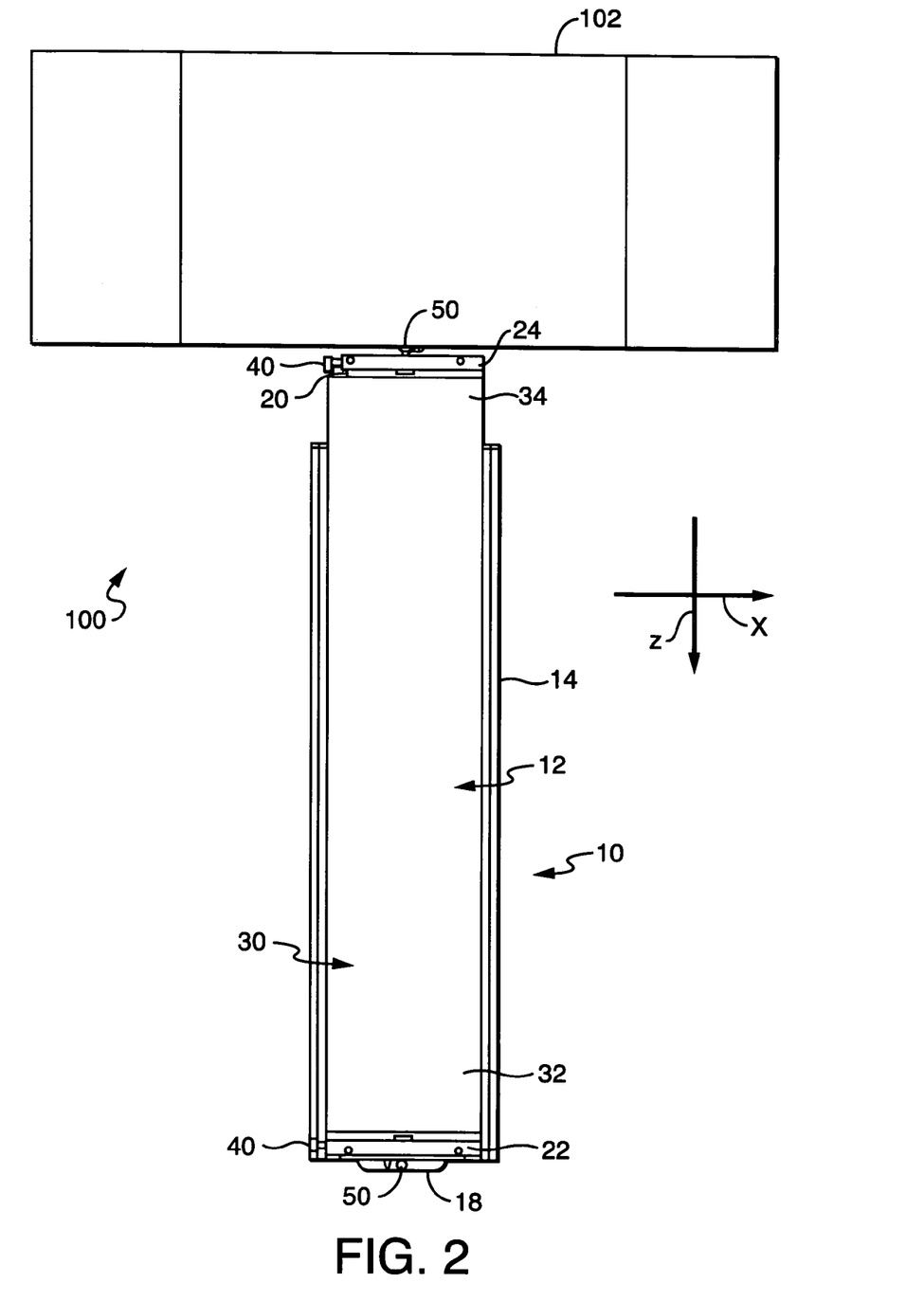
FIG. 2 is a top plan view of the patient table and the gantry of FIG. 1.
Figure 3:
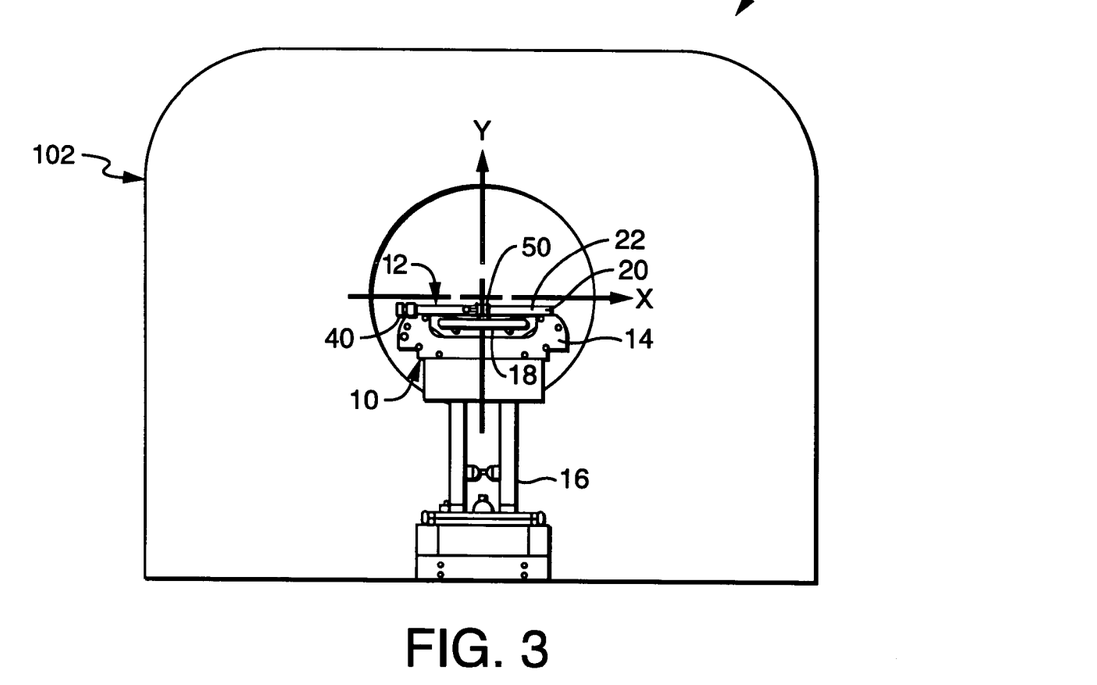
FIG. 3 is an end elevation view of the patient table and the gantry of FIG. 1.

Referring first to FIGS. 1 through 3, an x-ray tomography scanner system 100 is shown with an exemplary embodiment of a patient table 10 constructed in accordance with the present invention. Among other features and advantages, the patient table 10 of the present invention has an improved pallet assembly 12 that allows opposing ends 32, 34 of a longitudinally extending upper portion 30 of the pallet assembly 12 to each be laterally adjusted so that a patient lying on the pallet assembly 12 can be correctly positioned within an annular gantry 102 of the scanner system 100 and can be correctly positioned within a system for providing radiation therapy.

As is known to one skilled in the art of x-ray tomography scanning, the scanner system 100 includes the annular gantry 102 containing therein an x-ray source that projects a beam of x-rays toward a detector array on an opposite side of the gantry 102. During a scanning procedure, the annular gantry 102 and the components mounted thereon rotate about a center of rotation, which is parallel and aligned with a z-axis (isocenter) of a Cartesian coordinate system shown in FIG. 1. The x-ray beam is collimated to lie within in an x-y plane of the Cartesian coordinate system and pass through a patient lying on the patient table 10 within an opening of the gantry 102. The detector array within the gantry 102 senses the projected x-rays that pass through the patient and produces electrical signals that represent the intensity of the attenuation of the x-ray beam passing through the patient.

Although not shown, rotation of the gantry 102 and the operation of the x-ray source are governed by a control mechanism of the scanner system 100. The control mechanism includes an x-ray controller that provides power and timing signals to the x-ray source within the gantry and a gantry motor controller that controls the rotational speed and position of the gantry 102. A data acquisition system (DAS) of the control mechanism samples analog data from the detector array of the gantry 102 and converts the data to digital signals for subsequent processing. An image reconstructor receives the sampled and digitized x-ray data from the DAS and performs high speed image reconstruction, which is applied as an input to a computer which stores the image in a mass storage device.

The computer of the control mechanism of the scanner system 100 in turn receives commands and scanning parameters from an operator via an input device, such as a keyboard, and a video display allows the operator to observe the reconstructed image and other data from computer. The operator supplied commands and parameters are used by the computer to provide control signals and information to the DAS, the x-ray controller and the gantry motor controller.

The computer of the scanner system 100 can also be used to control operation of the patient table 10 to correctly position a patient through the central opening in the gantry 102. In particular, after the patient table 10 is correctly positioned with respect to the gantry 102, as shown in FIG. 1, the patient table 10 is operated to lift a patient vertically (parallel with the y-axis) to a desired position with respect to the rotation axis (z-axis) of the gantry before beginning a scanning procedure. During the scanning procedure, the patient table 10 is then operated to move a patient horizontally through the annular gantry 102 in a direction parallel with the rotation axis (z-axis) of the gantry.

Although not shown, it is intend that a patient table 10 constructed in accordance with the present invention can also be used for providing radiation therapy to a patient lying on the table. A pallet assembly constructed in accordance with the present invention is particularly useful for use with a radiation therapy system, such as the TomoTherapy Hi-Art system, in adjusting a patient's position if necessary to ensure radiation is directed at cancerous tumors and not healthy tissue within the patient.

Figure 4:
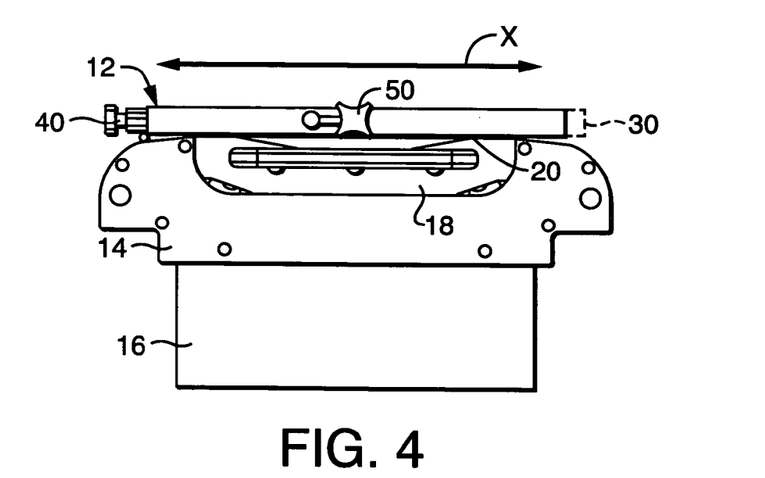
FIG. 4 is an enlarged end elevation view of the patient table of FIG. 1.
Figure 5:
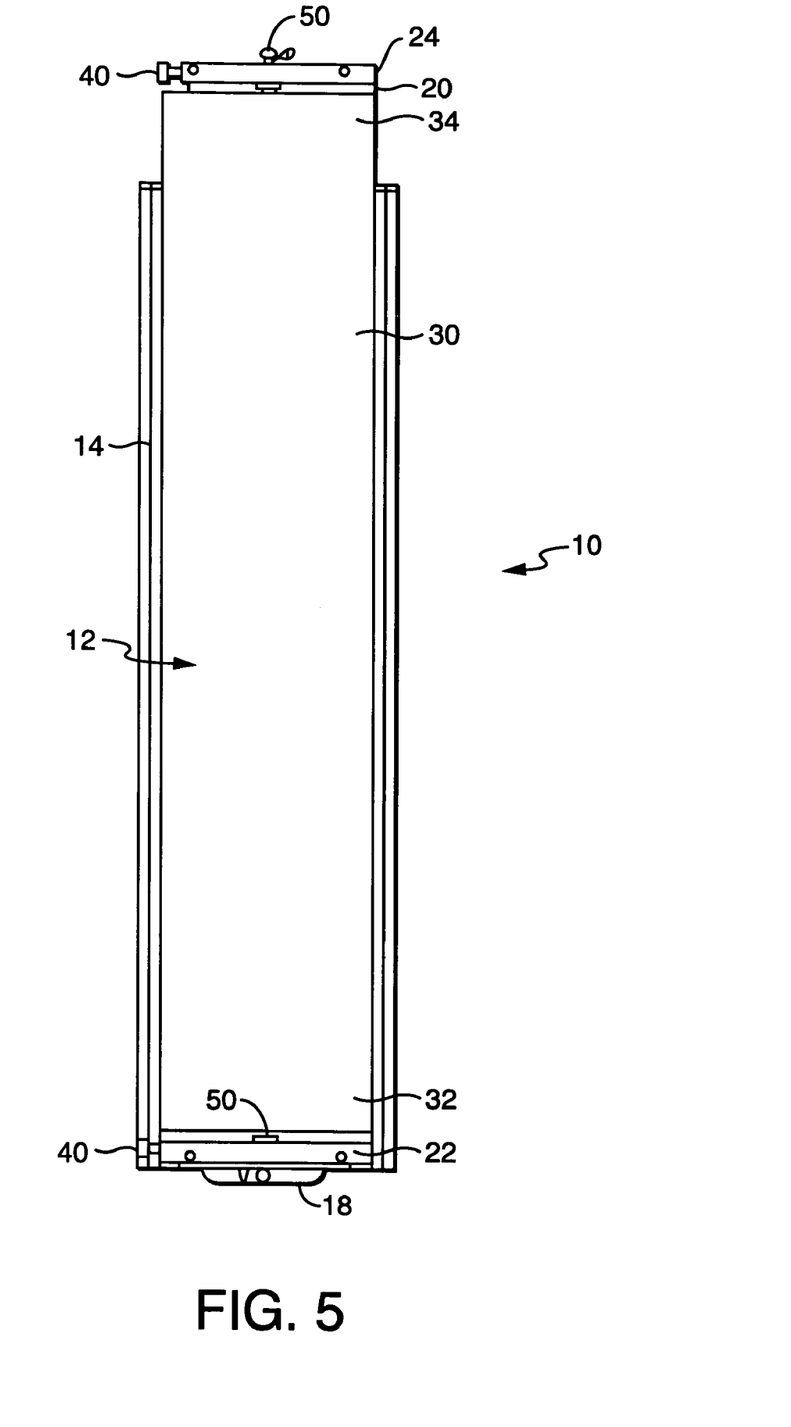
FIG. 5 is a top plan view of the patient table of FIG. 1.
Figure 6:
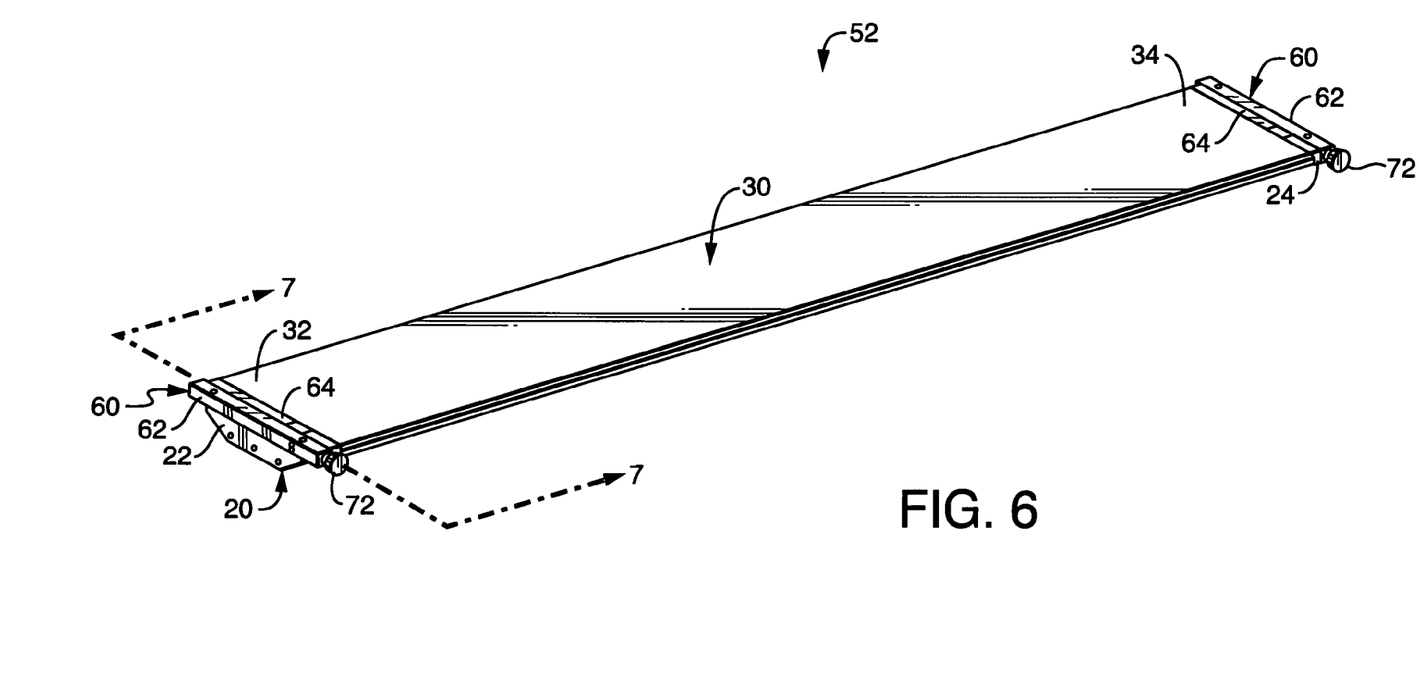
FIG. 6 is a top and end perspective view of another exemplary embodiment of a pallet assembly constructed in accordance with the present invention.
Figure 7:
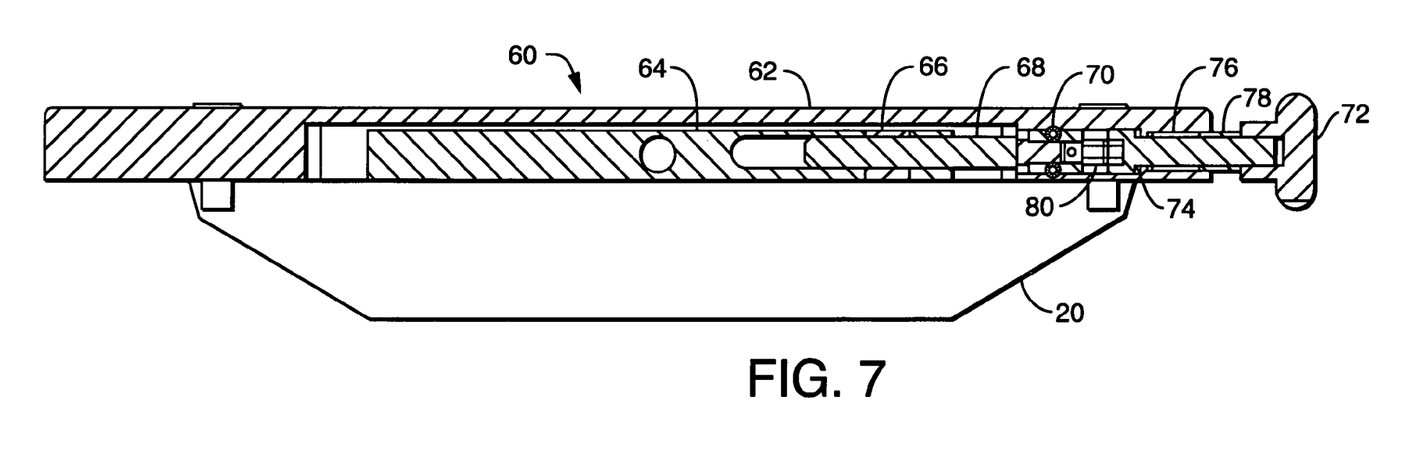
FIG. 7 is a sectional view of the pallet assembly taken along line 7—7 of FIG. 6.
Figure 8:
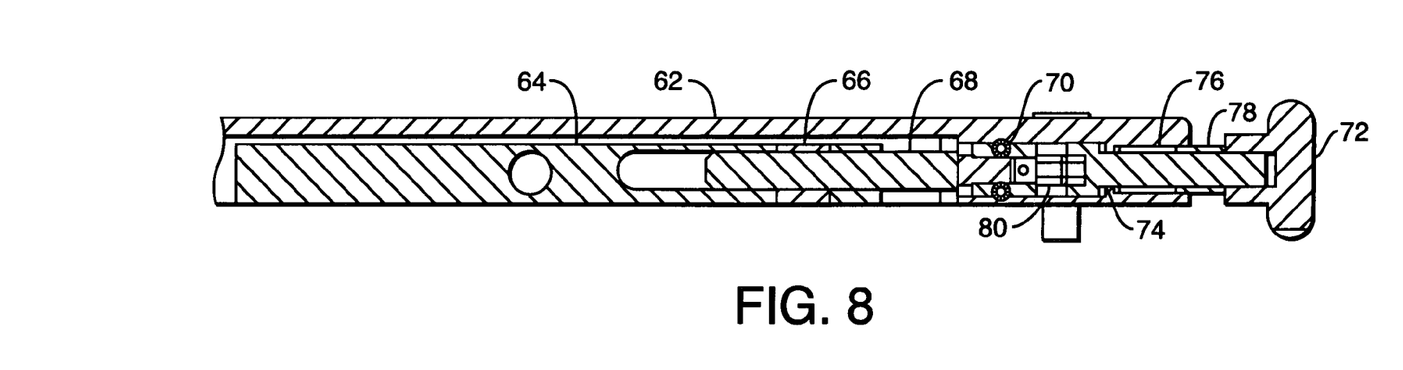
FIG. 8 is an enlarged sectional view of the pallet assembly of FIG. 6.
Figure 9:
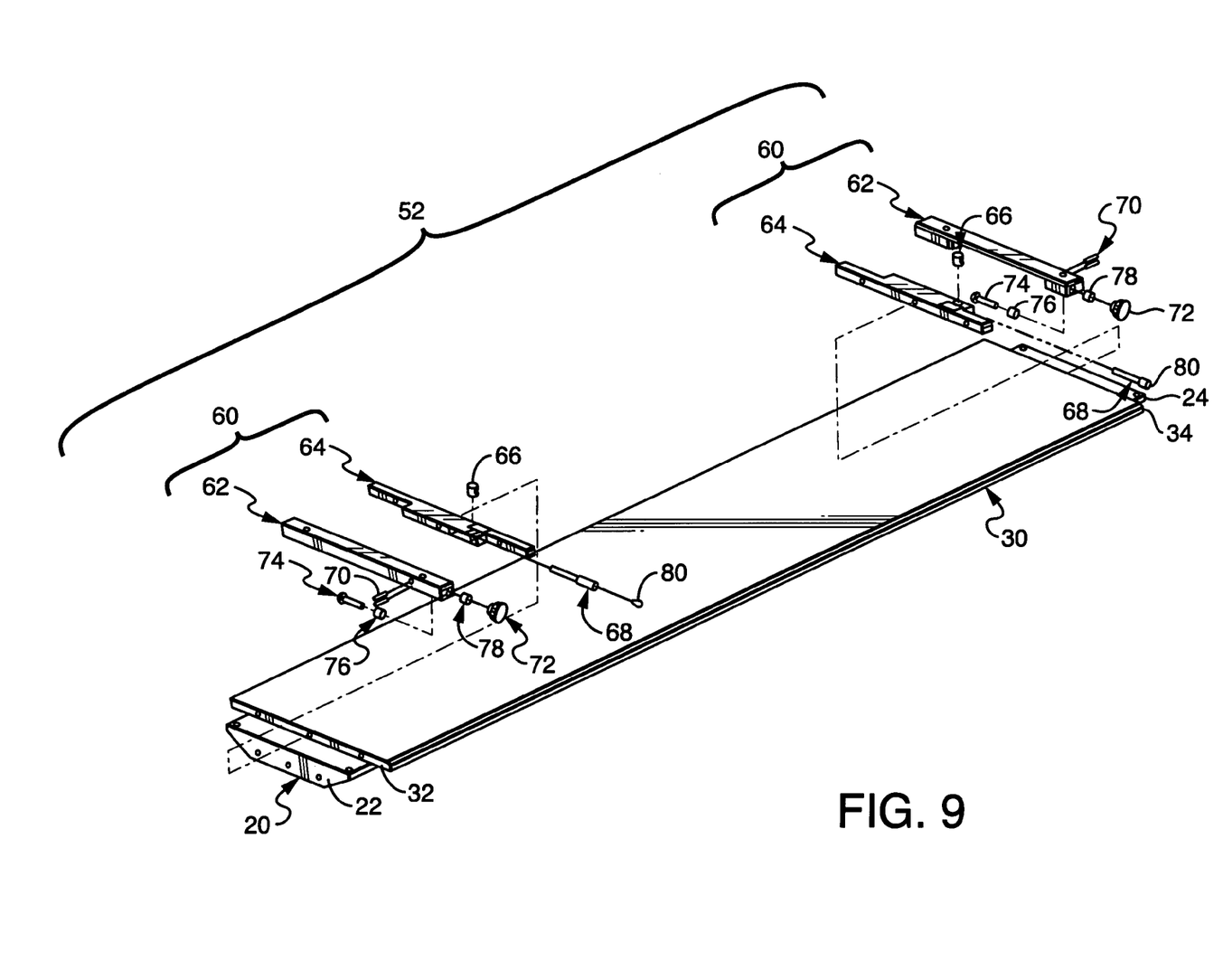
FIG. 9 is an exploded top and end perspective view of the pallet assembly of FIG. 6.

Referring also to FIGS. 4 and 5, the patient table 10 includes a table assembly 14 and the improved pallet assembly 12 is positioned on the table assembly 14. As shown, the table 10 is positioned with respect to the gantry 102 such that the elongated pallet assembly 12 extends parallel with the rotation axis (z-axis) of the gantry 102. The table 10 also includes a lifting apparatus 16 supporting the table assembly 14 and the pallet assembly 12. The lifting apparatus 16 is used to lift the table assembly 14, the pallet assembly 12 and a patient supported thereon, vertically (parallel with the y-axis) to a desired position with respect to the rotation axis (z-axis) of the gantry 102 before beginning a scanning procedure. The lifting apparatus 16 normally includes a cover assembly, but which is shown removed in FIGS. 1 through 3.

The elongated pallet assembly 12 is shaped and sized for a patient to lie thereon in alignment with the rotation axis (z-axis) of the gantry 102. The pallet assembly 12 includes a lower portion 20 (with "upper" and "lower" being made with reference to the y-axis in the figures) supported on a carriage 18 that is slidably mounted for longitudinal movement on the table assembly 14 (with "longitudinal" being made with reference to the z-axis in the figures). The lower portion 20, therefore, is longitudinally moveable with respect to the table assembly so that the pallet assembly 12 and a patient supported thereon can be extended to move the patient horizontally through the annular gantry 102 in a direction parallel with the rotation axis (z-axis) of the gantry. The lower portion 20, however, has opposing ends 22, 24 that are laterally fixed with respect to the table assembly 14 (with "opposing ends" being made with reference to the z-axis in the figures and "laterally" being made with reference to the x-axis in the figures).

The pallet assembly 12 also includes the longitudinally extending upper portion 30 that is longitudinally fixed with respect to the lower portion 20 of the pallet assembly and has opposing ends 32, 34 that are each laterally moveable with respect to the ends 22, 24 of the lower portion 20. Among other features and advantages, a pallet assembly 12 constructed in accordance with the present invention has opposing ends 32, 34 that are each laterally adjustable so that a patient lying on the upper portion 30 can be correctly positioned within the gantry 102 in a comfortable manner, and without being moved on the pallet.

As shown in FIGS. 1 through 5, the pallet assembly 12 can also be provided with adjusting mechanisms 40 for adjusting the lateral positions of the ends 32, 34 of the upper portion 30 of the assembly with respect to the ends 22, 24 of the lower portion 20, and locking mechanisms 50 for locking the ends 32, 34 of the upper portion 30 in position with respect to the ends 22, 24 of the lower portion 20.

In the exemplary embodiment of FIGS. 1 through 5, the lateral adjusting mechanisms 40 each include threaded nuts secured to the ends 32, 34 of the upper portion 30 and threaded bolts secured to the ends 22, 24 of the lower portion 20. The bolts are threadedly received by the threaded nuts, so that turning the bolts causes lateral movement of the ends 32, 34 of the upper portion 30 with respect to the ends 22, 24 of the lower portion 20.

In the exemplary embodiment of FIGS. 1 through 5, each locking mechanism 50 includes threaded nuts secured to the ends 22, 24 of the lower portion 20 and a threaded bolt extending through the threaded bolt and directed towards the ends 32, 34 of the upper portion 30. Turning the bolt through the nut causes the ends 32, 34 of the upper portion 30 to be locked in a lateral position with respect to the ends 22, 24 of the lower portion 20.

FIGS. 6 through 9 show another exemplary embodiment of a pallet assembly 52 constructed in accordance with the present invention. The pallet assembly 52 of FIGS. 6 through 9 is similar to the pallet assembly 12 of FIGS. 1 through 5 such that similar elements are provided with the same reference numerals. The pallet assembly 52 includes adjusting mechanisms 60 for adjusting the lateral positions of the ends 32, 34 of the upper portion 30 of the assembly 52 with respect to the ends 22, 24 of the lower portion 20.

Each lateral adjusting mechanism 60 includes first attachment brackets 62 secured to the ends 22, 24 of the lower portion 20 of the assembly 52 and second attachment brackets 64 secured to the ends 32, 34 of the upper portion 30 of the assembly 52. The second attachment brackets 64 have bushings 66 secured therein with screw threads receiving threaded lead screws 68, so that turning the lead screws causes the lead screws to be threaded through the bushings. Pin dowels 70 extend through the first attachment brackets 62 and secure the lead screws 68 in a lateral position with respect the first attachment brackets 62 so that, when the lead screws 68 are turned, the bushings 66 and the second attachment brackets 64 move laterally with respect to the first attachment brackets 62. Thus, upon the lead screws 68 being turned, the second attachment brackets 64 move laterally with respect to the first attachment brackets 62 so that the ends 32, 34 of the upper portion 30 of the assembly 52 move laterally with respect to the ends 22, 24 of the lower portion 20 of the assembly 52.

Each lateral adjusting mechanism 60 also includes an elongated socket member 74 extending through the first attachment bracket 62 and secured to a handle or knob 72. The elongated socket members 74 are arranged to be received on and engage hex heads 80 of the lead screws 68 of the first attachment brackets 64, so that turning the knobs 72 will turn the bolt and adjust the lateral positions of the ends 32, 34 of the upper portion 30 of the assembly 52.

Springs 76 and cylindrical spacers 78 are received on the socket members 74 and operate to normally bias the socket members 74 away from the lead screws 68 of the first attachment brackets 64 to prevent accidental turning of the lead screws 68. In order to adjust the lateral positions of the ends 32, 34 of the upper portion 30 of the assembly 52, the knobs 72 and the socket members 74 must first be pushed against the lead screws 68, and then turned to adjust the lead screws.

Figure 10:
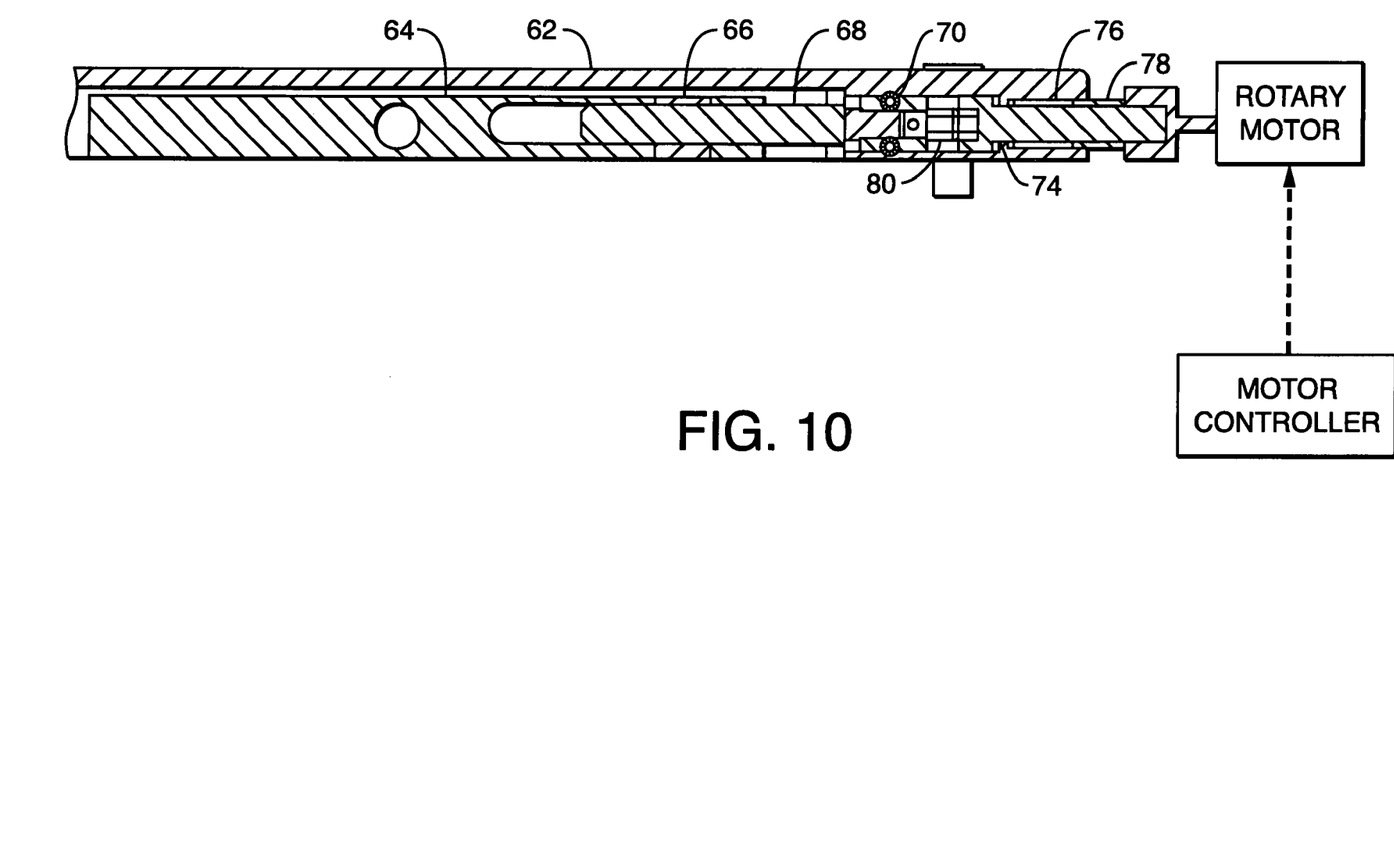
FIG. 10 is an enlarged sectional view of another exemplary embodiment of a pallet assembly constructed in accordance with the present invention.

FIG. 10 shows a portion of another exemplary embodiment of an adjusting mechanism 60 constructed in accordance with the present invention. The view in FIG. 10 is similar to the view in FIG. 8, and the adjusting mechanism 60 of FIG. 10 is similar to the adjusting mechanism 60 of FIGS. 6 through 9 such that similar elements are provided with the same reference numerals. The adjusting mechanism 60 of FIG. 10, however, includes a rotary motor and a motor controller for turning the elongated socket member 74 and the lead screw 68 of the adjusting mechanisms 60 and adjusting the lateral position of the end of the upper portion of the assembly with respect to the end of the lower portion.

While the patient table 10 and the pallet assemblies 12, 52 of the present invention are described and shown as being used with an x-ray tomography machine, the patient tables 10, 50 can also be used in other applications. In addition, while the pallet assemblies 12, 52 of the present invention are described and shown as being manually adjustably it should be understood that the table can be provided with motors (e.g., electrical stepper motors) for adjusting the lateral positions of the ends of the upper portion of the pallet assembly. Moreover, the pallet assemblies 12, 52 can be provided with control devices for controlling the motors.

It should be understood that the embodiments of the present invention described herein are merely exemplary and that a person skilled in the art may make variations and modifications to the embodiments described without departing from the spirit and scope of the present invention. All such equivalent variations and modifications are intended to be included within the scope of these invention as defined by the appended claims.

What is claimed is:

1. A patient table including a pallet assembly comprising:
   a longitudinally extending lower portion having opposing ends; and
   a longitudinally extending upper portion having opposing ends that are each laterally moveable with respect to the ends of the lower portion, wherein the pallet assembly further comprises lateral adjusting mechanisms connecting the ends of the upper portion of the assembly to the ends of the lower portion of the assembly, and the lateral adjusting mechanisms are manually operable.

2. A patient table according to claim 1, wherein the pallet assembly further comprises locking mechanisms for locking the ends of the upper portion of the assembly in lateral positions with respect to the ends of the lower portion.

3. A patient table according to claim 1, further comprising a table assembly supporting the pallet assembly and wherein the opposing ends of the lower portion of the pallet assembly are laterally fixed with respect to the table assembly.

4. A patient table including a pallet assembly comprising:
   a longitudinally extending lower portion having opposing ends; and
   a longitudinally extending upper portion having opposing ends that are each laterally moveable with respect to the ends of the lower portion, further comprising a table assembly supporting the pallet assembly and wherein the lower portion of the pallet assembly is longitudinally moveable with respect to the table assembly.

5. A patient table according to claim 4, wherein the pallet assembly further comprises lateral adjusting mechanisms connecting the ends of the upper portion of the assembly to the ends of the lower portion of the assembly.

6. A patient table according to claim 5, wherein the lateral adjusting mechanisms include motors for causing lateral movement of the ends of the upper portion of the pallet assembly.

7. A patient table according to claim 6, wherein the lateral adjusting mechanisms include a controller for controlling the motors.

8. A patient table according to claim 4, wherein the upper portion of the pallet assembly is longitudinally fixed with respect to the lower portion of the pallet assembly.

9. A patient table according to claim 4, further comprising:
   locking mechanisms for locking the ends of the upper portion of the assembly in lateral positions with respect to the ends of the lower portion.

* * * * *